United States Patent [19]

Watt et al.

[11] 3,980,074

[45] Sept. 14, 1976

[54] DEVICE FOR THE ADMINISTRATION OF POWDERS

[75] Inventors: Peter Ridgway Watt, Ewhurst; Harold George Wilkinson, Goring-by-Sea, both of England

[73] Assignee: Beecham Group Limited, Great Britain

[22] Filed: Oct. 16, 1975

[21] Appl. No.: 622,802

Related U.S. Application Data

[63] Continuation of Ser. No. 487,714, July 11, 1974, abandoned.

[30] Foreign Application Priority Data

July 18, 1973 United Kingdom............... 34273/73

[52] U.S. Cl................................ 128/2 A; 128/208; 128/266; 222/193
[51] Int. Cl.²........................................... A61B 6/00
[58] Field of Search................... 222/193, 195, 464; 128/206, 208, 265, 266; 128/2 A

[56] References Cited

UNITED STATES PATENTS

| 310,444 | 1/1885 | Kibele.................................. 128/266 |
| 2,517,482 | 8/1950 | Hall................................. 128/208 X |
| 2,642,063 | 6/1953 | Brown................................ 128/206 |
| 2,672,865 | 3/1954 | Willis................................. 128/206 |
| 3,565,071 | 2/1971 | Cobb et al. ..................... 128/208 X |
| 3,777,742 | 12/1973 | Aumiller et al..................... 128/2 A |

FOREIGN PATENTS OR APPLICATIONS 1,118,341 7/1968 United Kingdom................. 128/266

*Primary Examiner*—Robert B. Reeves
*Assistant Examiner*—Joseph J. Rolla

[57] ABSTRACT

A device for the oral inhalation of large quantities of finely divided powders for bronchoradiography has an elongate housing attached to a container and having air vents situated so that the intake of breath by the user of the device causes a vortex of air within the housing.

12 Claims, 7 Drawing Figures

DEVICE FOR THE ADMINISTRATION OF POWDERS

This is a continuation of Ser. No., 487,714 filed July 11, 1974, now abandoned.

This invention relates to a device for oral inhalation of finely divided powders and in particular for use in bronchoradiography.

Radiography of the bronchial tract is of great diagnostic value in the investigation of disorders of that region, and involves the administration of a radio opaque substance to the lungs of a patient prior to radiography. It is known that such substances may be administered for example as aqueous solutions or dispersions or as a liquid aerosol. However the most advantageous method of administration comprises the direct insufflation of the radio-opaque material in the form of a powder of sufficiently small particle size to reach the fine airways of the lung. Devices are known for the administration of powders by inhalation, but many require an additional source of power besides the patients inhalation to blow the powder out of the device. Examples of such additional sources of power include, for example, a rubber aqueeze bulb (see Belgian Pat. No. 764,576) or a source of gas under pressure (see British Pat. No. 1,305,172). In such devices it is difficult to synchronise the patient's inhalation with the operation of the additional source of power. Other inhalation devices which are activated solely by the users' inhalation are described in British Pat. Nos. 1,118,341, 1,182,779, 1,122,284, 1,295,081, 1,301,856, U.S. Pat. No. 3,635,219, Belgian Pat. No. 781,102 and our British Pat. No. 36428/72.

All these devices, however, are designed for oral administration of relatively small quantities of powder at a time and are insufficient for the requirements of radiography, in which a total powder charge in the range 5 – 15 grams may be required.

We have now produced an inhalation device capable of handling these larger amounts of powder.

According to the present invention, there is provided a device for the oral inhalation of powders, which device comprises a hollow elongate housing, an outlet at one end thereof adapted for application to the mouth, the other end communicating with a container for powder; the container having one or more air inlet vents adapted to direct incoming air into a turbulent stream within the container; said housing having air inlet vents adapted to direct incoming air into a vortex within the housing; whereby the intake of breath by the user of the device causes powder within the container to be fluidised, to pass into the vortex of air in the housing and thence through the outlet to the mouth of user.

One embodiment of the invention will now be illustrated with reference to the accompanying drawings wherein.

Figure 1:
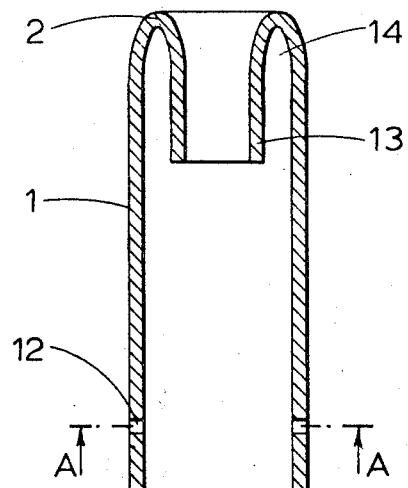
FIG. 1 is a cross-section through the major axis of an oral inhalation device in accordance with this invention.
Figures 2, 3:
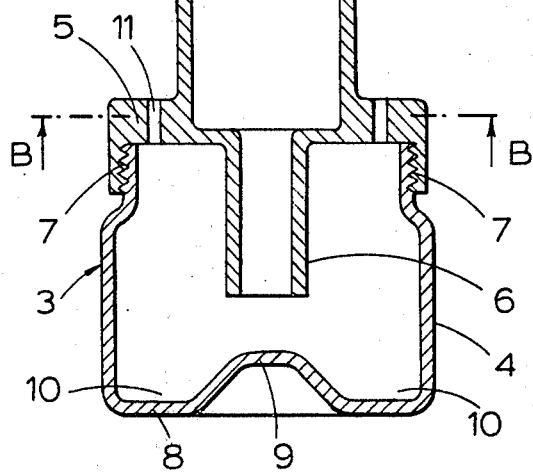
FIG. 2 is a cross-section through the line A—A of FIG. 1.
FIG. 3 is a cross-section through the line B—B of FIG. 1.

Referring to the drawings, the inhalation device comprises a hollow elongate housing 1, made of plastic material. One end of the housing is provided with an outlet 2 of restricted diameter which serves as a mouthpiece. The other end of the housing 1 is provided with a powder container 3 comprising a body 4 and a flange 5, the latter being integral with the housing; and an extension 6 of the housing protrudes into the container. The container body 4 and flange 5 are joined by means of screw thread 7. The base 8 of the container has a central protuberance 9 producing an annular trough 10. The flange 5 of the container is provided with a number of air inlet vents 11, drilled at a constant angle to the longitudinal axis of the housing 1, this angle preferably being in the range 40°–85°. The configuration of these vents is shown more clearly in FIG. 3. The housing 1 also has inlet vents 12 again drilled tangentially as shown in FIG. 2. The vents 12 may be disposed at an angle from 10°–80° to a radius of the housing. The outlet 2 is also provided with an extension 13 which projects into the housing 1, leaving an annular space 14.

In operation of the device, the housing 1 is maintained in a vertical position.

Powdered medicament is placed in the container body 4, which is then assembled onto the flange 5 by means of the screw thread 7. The patient inserts the portion of the housing in the vicinity of the outlet vent 2 into his mouth and inhales. Air is drawn into the device through the inlet vents 11 and 12. Air entering through the inlet vents 12 causes a vortex to develop within the housing 1. Air entering the inclined inlet vents 11 passes into the powder container 3, thereby fluidising its contents and produces a vortex motion of air within the container 3. The powder is entrained in this circulating air-stream and thus prevented from passing straight up the extension 6. The heavier particles of powder are flung outwards against the walls of the container 3, but the finer particles will be drawn through the extension 6 and into the circulating air-stream present in the interior of the housing 1. As the heavier particles circulate in the container 3 they are subject to attrition on the side walls of the container until they are sufficiently reduced in size to escape through the extension 6. The powder circulating within the housing 1 is drawn towards the outlet vent 2 and approaches a second classification stage provided by the outlet extension 13 and the annular space 14. Again only the finer particles in the stream are drawn through the outlet 2 and into the patient's lungs. Coarser particles are held back within the space 14 until they are reduced in size by attrition sufficiently to also escape through the central extension 13 and thence through the outlet vent 2.

In this embodiment, the base 8 of the container 3 has a central protuberance 9. This provides the annular trough 10 for the powder and reduces the likelihood of a dense cloud of powder passing towards the outlet vent 2 at the onset of inhalation.

Figure 4:
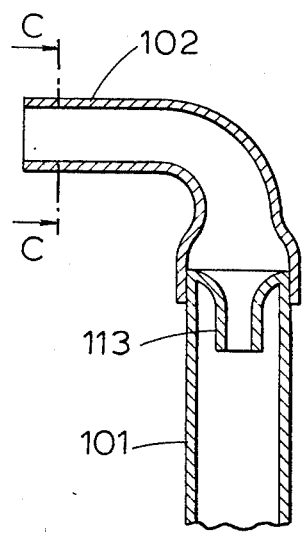
FIGS. 4 and 5 are cross-sections through upper portions of two alternative devices in accordance with this invention.
Figure 5:
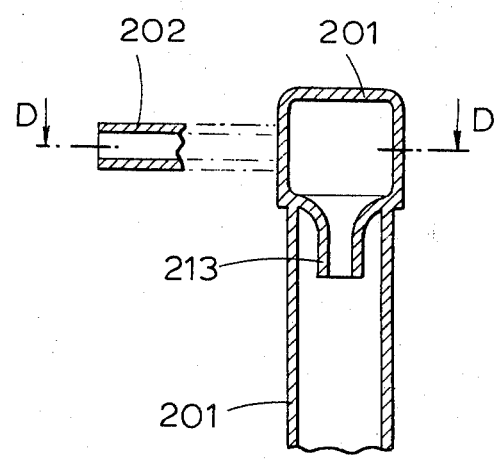
Figure 6:
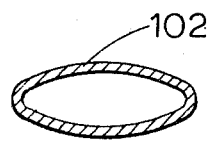
FIG. 6 is a cross-section through the line C—C of FIG. 4.

Two alternative forms of outlet are depected in FIGS. 4 and 5. In FIG. 4 the outlet 102 is in the form of a curved tube attached to the upper end of the housing 101. A classifier in the form of an extension tube 113 is again provided within the housing 101. The end of the outlet 102 is elliptically shaped, as shown in FIG. 6 for easy application to the mouth. With the configuration shown in FIG. 4, the device can be held upright whilst the patient inhales horizontally through the outlet 102.

Figure 7:
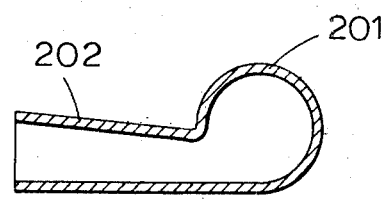
FIG. 7 is a cross-section through the line D—D of FIG. 5.

In FIG. 5, the outlet of the device is in the form of an extension 202 integral with and tangential to the upper portion of the housing 201. The configuration of the extension 202 is shown more clearly in FIG. 7. The classifier is in the form of an inner extension tube 213. The end of the outlet 202 is again elliptically shaped for insertion into the mouth.

In alternative embodiments of devices according to this invention, the powder container may be separable into two parts at any point and may be adapted to be reassembled by alternative means to that illustrated above, for example by a snap-on/snap-off locking mechanism. If the container is separable so that one half is in the form of a flange integral with the housing, as shown above, then the flange may be adapted to fit onto a standard screw-top bottle in which the powder may be stored prior to use.

The device of this invention also has one or more inlet vents in the container adapted to permit the passage of a turbulent stream within the container. These inlet vents may be in the sides or the top of the container. In order to produce the required turbulent stream, these inlets may be angled as described above, or they may be positioned adjacent internal angled barriers so that incoming air is directed to a circular path. Similarly the inlet vents in the elongate housing may be angled or they may be positioned adjacent internal angled barriers. Preferably the inlet vents in the housing are positioned approximately midway between the outlet and the powder container.

We claim:

1. A device for the insufflation of powders in a quantity sufficient for radiography comprising a container for powder removably attached to an elongated housing having a passage formed therein, said passage communicating internally at one end thereof with the container for powder and at the other end thereof terminating in a mouthpiece provided in the housing, first air inlet means for producing turbulent air flow in the container, being provided in the housing or the container for powder, a protuberance arranged centrally in the base of the container to prevent a powder when present within the container from being fluidized into a dense cloud at the onset of insufflation and second air inlet means for directing incoming air into a vertical motion within the passage, said second air inlet means being provided in the housing; and means for classifying powder adjacent the interior walls of the passageway between the mouthpiece and the second air inlet means.

2. A device according to claim 1 wherein the elongated housing is cylindrical and the second air inlet means are vents disposed at an angle of between 10° and 80° to the radius of the housing midway between the mouthpiece and the container.

3. A device according to claim 1 wherein the end of the mouthpiece is elliptical in cross-section.

4. A device according to claim 1 in which the amount of powder is sufficient for radiography and is in the range of 5–15 g.

5. A device according to claim 1 wherein the first air inlet means are vents in the top of the container, which are arranged in a concentric formation.

6. A device according to claim 5 wherein the vents are disposed at an angle of from 40° to 85° to the longitudinal axis of the housing.

7. A device according to claim 1 which further comprises means for allowing only finer powder particles from the container into the housing.

8. A device according to claim 7 wherein the means comprises constricting the cross-sectional area of the passage to be smaller than that of the container at the intersection of the passage and container.

9. A device according to claim 1 wherein the mouthpiece is in the form of a tube having its longitudinal axis at right angles to that of the housing.

10. A device according to claim 9 wherein the mouthpiece is in the form of a curved tube attached to the upper end of the housing.

11. A device according to claim 9 wherein the mouthpiece is in the form of an extension integral with and tangential to the upper portion of the housing.

12. A bronchoradiographic device suitable for the insufflation of powders in an amount sufficient for radiography, which comprises a hollow elongated housing having an outlet vent at one end thereof for reception into the mouth, a container for the powders removably attached to the other end of the housing and having air inlet vents to direct incoming air into a turbulent stream within the container and a central protuberance arranged to prevent a dense cloud of fluidised powder from passing towards the outlet at the onset of insufflation, said housing air inlet vents directing incoming air into a vortex within the housing; whereby the intake of breath by the user of the device causes powder within the container to be fluidised, to pass into the vortex of air in the housing, and thereafter through the outlet vent to the mouth of the user and means for classifying said fluidised powder so that large particles are prevented from passing through the outlet vent.

\* \* \* \* \*